United States Patent
Prunier et al.

[11] Patent Number: 5,275,717
[45] Date of Patent: Jan. 4, 1994

[54] PROCESS FOR THE MANUFACTURE OF PROSTHETIC ELEMENTS AND ELEMENTS PRODUCED THEREBY

[76] Inventors: Pascal Prunier, Le Martinet, Route de Mazan, F-84200 Carpentras; Jean Blanc, L'Oratoire, Avuenue Gabriel-Peri, F-30400 Villeneuve-les-Avignon; Laurent Isnard, 28, bd. Paul-Floret, F-84000 Avignon; Catherine Gerard, Sous-la-Maltiere, Marigny-le-Cahouet, F-21150 Venarey-les Laumes; Maurice Cagniart, Le Martinet, Route de Mazan, F-84200 Carpentras; Regis Ruiz, 32A, chemin des Cent-Ecus, F-21000 Dijon, all of France

[21] Appl. No.: 778,061
[22] PCT Filed: Jun. 5, 1990
[86] PCT No.: PCT/FR90/00391
  § 371 Date: Jan. 30, 1992
  § 102(e) Date: Jan. 30, 1992
[87] PCT Pub. No.: WO90/14801
  PCT Pub. Date: Dec. 13, 1990

[30] Foreign Application Priority Data
Jun. 5, 1989 [FR] France ............... 8907404

[51] Int. Cl.$^5$ ............................................. C25D 11/04
[52] U.S. Cl. ............................................. 205/324
[58] Field of Search ................................ 205/324

[56] References Cited

U.S. PATENT DOCUMENTS

| | | | |
|---|---|---|---|
| 4,145,764 | 3/1979 | Suzuki et al. | 3/1.9 |
| 4,556,389 | 12/1985 | Ueno et al. | 433/306 |
| 4,746,532 | 5/1988 | Suzuki et al. | 437/3 |

FOREIGN PATENT DOCUMENTS

| | | |
|---|---|---|
| 0211676 | 2/1987 | European Pat. Off. . |
| 2318617 | 2/1977 | France . |
| 8700030 | 1/1987 | World Int. Prop. O. . |

Primary Examiner—T. M. Tufariello
Attorney, Agent, or Firm—Sandler, Greenblum & Bernstein

[57] ABSTRACT

Process for the manufacture of dental or maxillo-facial prostheses, particularly endo-osseous prostheses or pivots, in which a layer of pure aluminum is deposited on a conductive substrate, preferably a metal, which forms the core of the prosthesis. The aluminum layer is obtained by electrochemical deposition of pure aluminum with non-aqueous electrolyte base of the type which has an aluminumorganic complex bath. The layer is then oxidized by anodization such that an alumina layer which is sealed and electrically insulated, is obtained, separating the core and the biological tissues surrounding the prosthesis.

20 Claims, 1 Drawing Sheet

PROCESS FOR THE MANUFACTURE OF PROSTHETIC ELEMENTS AND ELEMENTS PRODUCED THEREBY

BACKGROUND OF THE INVENTION

1. Field of the Invention

The invention relates to the processes for the manufacture of prosthetic elements, such as dental and maxillo-facial elements, and elements produced by such processes.

2. Discussion of Background Information

A number of materials were tested for the purpose of reconstructing or repairing hard biological tissues, namely bones or teeth. These materials, often called biomaterials, should have appropriate mechanical properties and not cause chemical reactions detrimental for tissues coming into contact with a prosthesis made with these materials.

In this respect, the qualities of metal oxides, in particular those of alumina, $Al_2O_3$, the principal oxide of aluminum are known. Indeed, alumina is an extremely chemically stable compound, and is therefore considered as being inert in a biological medium. In addition, the hardness of alumina, four to five times higher, depending on its state, than the hardness of titanium alloys makes it a biomaterial which is mechanically superior to widely used titanium alloys. Moreover, the cost of titanium alloys is high compared with that of alumina. Therefore, alumina is particularly advantageous for the production of prostheses for use in a biological medium.

Known processes for manufacturing alumina prostheses, or prostheses coated with alumina, do however have serious disadvantages. Indeed, at present, it is now known how to use alumina except in the form of deposited or projected ceramics, i.e., the production of a layer of alumina either consists in the sintering of powders which are then amalgamated or in a thermal spraying process (by means of an electron torch, for example). These techniques, applied to the coating of prostheses or implants are described for example in the U.S. Pat. No. 4,556,389, in EP-211 676, in FR-2 318 617, and in International Application WO 87/00030.

However, these techniques are disadvantageous because:

either the layer of alumina deposited on the prosthesis is thin, and the porosity of the ceramic causes a risk of bacterial invasion which could lead to an infection, or the layer is thick, around several tenths to several millimeters, and is fragile, and brittle, in spite of a porosity liable to promote the osteogenesis (regeneration of the bone around the prosthesis) without risk of infection.

Moreover, in both cases, the interface between the prosthesis and the layer of sintered or sprayed alumina is not unalterable since there only exists a mechanical retention between these two media. The layer of alumina is therefore not particularly adhesive.

Finally, should be noted that sintering and thermal spraying are not adapted to the deposit of ceramics on complex shapes, such as a threading, that occur frequently on prostheses or implanted prosthetic elements. These processes result in heterogeneous deposits of varying thickness covering the shapes. Moreover, even if it remains possible to reshape a profile in a layer of alumina ceramic which is sufficiently thick, the hardness of this oxide makes the work difficult and not very accurate.

SUMMARY OF THE INVENTION

The object of the invention is to remedy all these disadvantages by proposing a manufacturing process of elements for dental or maxillo-facial prostheses of the endo-osseous implants or pivot type, by which a layer of aluminum is deposited on a conductive substrate, notably a metal, for forming the core of a prosthesis or the core of a prosthetic element. The layer of aluminum is obtained by the electrochemical deposit of pure aluminum with a non-aqueous electrolyte base of the type which has an aluminum organic complex bath. This layer of pure aluminum is thereafter oxidized by anodization in a known manner until a layer of sealed and electrically insulating alumina is obtained separating the substrate and the biological tissue surrounding said prosthesis.

The process in accordance with the invention enables the use of all the previously known qualities mentioned of implanted alumina coated prostheses without the drawbacks. The superficial layer of pure alumina obtained on the substrate forming the core of a prosthesis or a prosthetic element is intimately linked with this substrate, which is not the case with a layer of sintered or sprayed ceramic. In particular, it is established that the adherence of aluminum deposited by non aqueous electrochemical means on steel is stronger than the shearing strength of the layer of aluminum itself. Moreover, the partial anodization of this last layer enables a superficial layer of alumina to be obtained which strongly adheres to the subjacent layer of aluminum.

This essential property of an anodized aluminum galvanic coating forms the main contribution of the invention and the consequences of an intimate adherence between the substrate and the superficial layer of alumina are of a mechanical and biological order:

first, the fragile area between the superficial layer of alumina and the core of the prosthesis, no longer exists; consequently, the core undergoes the stresses that are applied to it in a more equal way which increases its solidity and durability then, bacterial invasion becomes unlikely because subjacent layer of pure non anodized aluminum does not create a distinct interface between the superficial layer of alumina and the core of the prosthesis, this interface usually being the place where the bacterial concentration is the most important in the case of a sintered or sprayed layer of ceramic.

In an unexpected and complementary way, it is noted that thickness of the layer of pure alumina that is created on the surface of the prosthesis can be less than a layer of alumina ceramic deposited by sintering or thermal spraying and offering the same qualities of tightness and electrical insulation. The pure alumina is less porous than an alumina ceramic for obvious reasons connected with production methods. The porosity of a layer of ceramic is bad for its dielectric behaviour (insulation voltage), while a layer of pure alumina 50 microns thick offers an insulation voltage of about 1000 volts in a dry medium (which is quite enough when it is in a moist medium, in particular biological, where this voltage is lower).

In this way, we avoid all the electrical effects that might exist between the conducting materials present nearby in the implanted prosthesis, namely those forming other prostheses or another element of the said prosthesis, and the conductive substrate forming the core.

It should be noted that in the usual case of implanted prostheses made with a metal alloy and in particular with a titanium alloy, it is necessary, to avoid an electrical phenomena, to make all the elements of the prosthesis with this same material, which is generally very expensive; the method in accordance with the invention enables the use of a cheap conductive substrate to make the core, the layer of anodized aluminum in accordance with the invention being fully insulating with regard to the electrical voltages that might occur between this core and the outer conductive materials.

BRIEF DESCRIPTION OF THE DRAWINGS

Other characteristics and advantages of the manufacturing method in accordance with in invention will appear clearer from the description to follow of a preferred, non limitative method for the application of this process, referring to the attached drawing in which.

It should be noted that the figures are given as a schematic illustration of the invention and are by no means intended to indicate the scale or the proportion concerning the shown elements.

DESCRIPTION OF THE PREFERRED EMBODIMENTS

In accordance with these figures, a dental prosthesis 1, intended to replace a missing tooth, is composed of an implant 2 forming a root substitution on which a pivot 3 is fixed which is itself covered with an artificial part 4 restoring the crown of the tooth. In accordance with the invention, the implant 2 and the pivot 3 can both have a conductive core covered with a layer of pure alumina, but, so as to make the description clear, we will describe the special example of an implant 2 of titanium alloy and a pivot 3 made in accordance with the invention process.

Figure 1:
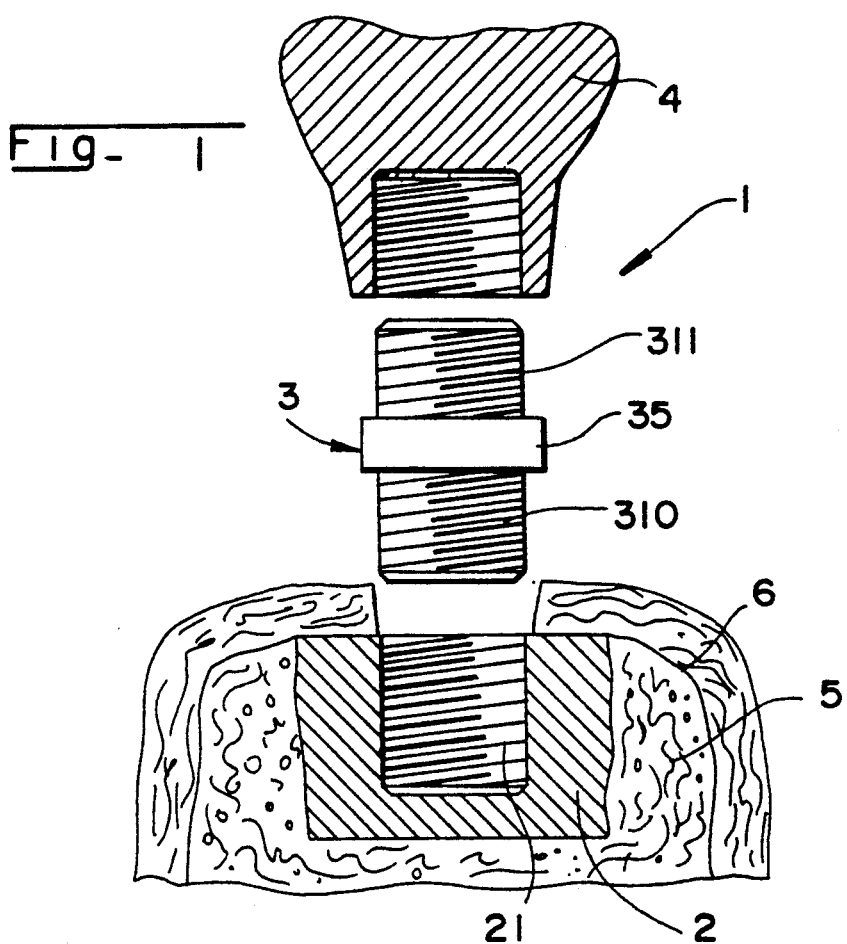
FIG. 1 shows a longitudinal cutaway view of the core of a dental prosthesis.

In accordance with FIG. 1, the pivot 3 comprises a conductive core 31 which can be, in particular, a metal with suitable mechanical characteristics (stainless steel, "super alloy", memory metal) or a highly resistant non-metallic body (carbon-carbon compound for example).

The core 31 is cylindrical and has two threads 310 and 311, the thread 310 allowing to screw the pivot 3 in the cavity 21 provided for that purpose inside the implant 2 and the thread 311 allowing to screw the artificial part 4 forming the crown of the tooth.

These threads 310 and 311 are made, in accordance with a preferred embodiment of the invention, before any deposit of aluminum on the core 31 which procures the very important advantage of facilitating the boring of the pivot 3.

It should be noted that in this embodiment of the invention, it is easy to make the boring automatic or, in a profitable and known manner, to make the core 31 of the pivot 3 by using prosthesis techniques called 'casting", which consists in realizing a mold in which the metal or material forming the core 31 is cast.

Figure 2:
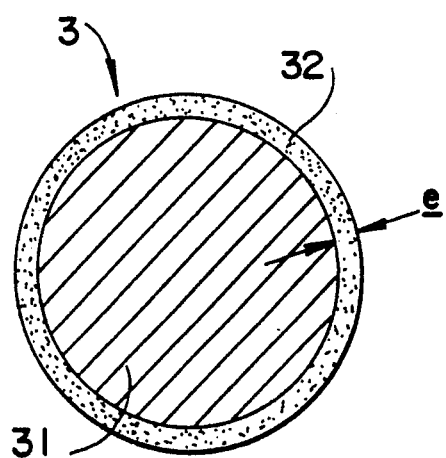
FIG. 2 shows the cross section of a pivot forming said prosthesis after the deposit of a layer of aluminum.

Once the threads 310 and 311 are obtained, in accordance with FIG. 2, a deposit of aluminum is made on the core 31 in such a manner that a coat of pure aluminum 32 is obtained, of a thickness e.

This deposit, according to a preferred embodiment of the invention, is a deposit carried out using a galvanizing method with a non-aqueous electrolyte base of the type which has an aluminumorganic complex bath; for example, it is possible to use the process commercially known under the name of "SIGAL" ®. The use of a galvanizing process explains the need to have a conductive material to make the core 31 of the pivot 3.

The main characteristic of the "SIGAL" ® process is to allow the creation of a relatively thick layer of pure aluminum (electrochemical refining effect); on any conductive material. The thickness e reached at present is approximately 300 microns, which is to be compared with the several micons thickness obtained with competitive depositing processes. But it has been shown that a layer of aluminum that is too thin does not allow a layer of alumina sealed created after oxidation. The determined seal limit for a layer of pure alumina made on a dental prosthesis 1 is 12 microns and the depositing processes competing with the SIGAl ® method allow a layer of alumina to be obtained of only 5 microns thick.

Figure 3:
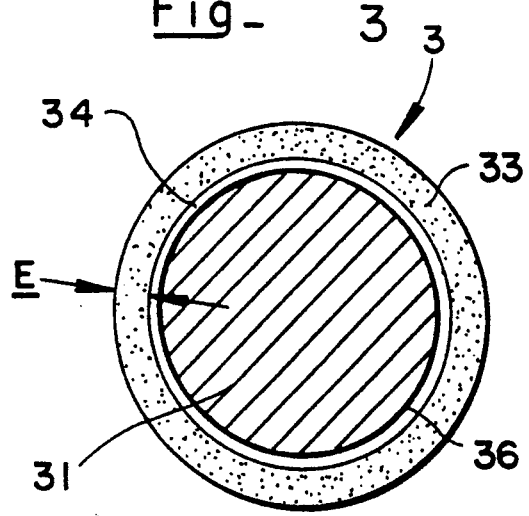
FIG. 3 shows the cross section of a pivot forming said prosthesis after the hard anodization of the layer of aluminum.

The process in accordance with the invention, in that is preferably incorporates the SIGAL ® method of depositing aluminum on a conductive material, enables, in accordance with FIG. 3, a layer of pure alumina 33 to be created by partial or total oxidation of the layer of aluminum 32. This oxidation more generally results from an anodizing process, which consists of an intense chemical treatment. Preferably a hard anodization process is used which increases the capacity of resistance to wear and offers a better aptitude to friction. In this case, it is preferable to create a layer of pure alumina 33 on the core 31 which is perfectly sealed and electrically insulating, forming an inert screen between this core 31 and the external biological medium. Other anodizing techniques can also be used and, particularly if the corrosion resistance of the aluminum coating itself is to be reinforced, it will be useful to use chromic or sulphuric anodization operations. This step can be followed by hydrating in a controlled manner the anhydrous oxide film produced by the anodization. This hydration is not used in the case of hard anodization which remains the technique preferably used for obtaining a thick layer of alumina 33.

It should be noted that the thickness E of the alumina layer 33 can reach approximately twice the thickness e of aluminum layer 32. This is due to the progressive swelling and penetration of the layer of alumina 33 during anodization. To obtain a layer of alumina 33 of thickness E, a layer of aluminum 32 with a thickness at least equal to $e = E/2$ must always be available.

In this way, if 150 microns of pure aluminum are deposited by galvinizing means, a layer of alumina 33 can be obtained with a thickness E of 300 microns. This thickness greatly exceeds the 12 microns necessary for the biological sealing of the pivot 3.

Preferably, the thickness of the layer of alumina 33 is approximately 50 microns, which corresponds to an experimentally determined optimum.

Indeed it has been shown that two problems may disturb the mechanical qualities of the layer 33:

first of all, if the layer of alumina 33 is too thick the alumina crystals forming the layer 33 are too large which hinders the superficial hardness and causes an undesirably porosity.

then, if after the deposit of a thick layer of aluminum 32, a layer of alumina 33 is created within the above mentioned limit, the same disadvantage occurs.

In a complementary manner, the process in accordance with the invention is characterized in that a layer of aluminum 32 is deposited which has a thickness slightly greater than a value equal to half of the layer of alumina 33 that we wish to obtain.

In this way, there is always between the layer of alumina 33 and the core 31 an intermediate layer 34 of aluminum with a relatively small thickness in comparison with that of the alumina 33. To obtain 50 microns of alumina, in a preferred embodiment of the invention, 30 to 40 microns of aluminum are deposited which, after oxidation, provide an intermediate layer 34 with a thickness of between 5 and 15 microns. This particular arrangement of the process in accordance with the invention is necessary if the adherence of the layer of alumina 33 on the core 31 is to be guaranteed without the disadvantages linked with a layer of ceramic made from sintered or spread alumina adhering by simple mechanical retention on the core 31.

In an unexpected manner, it should also be noted that the layer of aluminum 32 deposited by the SIGAL ® process, and the layer of alumina 33 obtained by anodization of a part of the sale layer 32 perfectly match the complex reliefs present on the core 31 and in particular the threads 310 and 311.

This considerable advantage of the process in accordance with the invention therefore, enables the manufacture of elements of a prosthesis 1, such as a pivot 3 or an implant 2, without having to bore them following the deposit of alumina.

In addition, the thickness of the layer of alumina 33 is consistent over the whole surface of the core 31 without covering the reliefs or uncovered spaces. In this way, prosthesis elements are created which can be precision bored and their reproduction, if necessary, in the event of deterioration, is easy. It should be noted that the use of pivots 3 or implants 2 that are insulated according to the invention process enables them to be replaced easily without fear of undesirable electrical effects; this is one of the main advantages of the insulating prostheses 1 in comparison with titanium alloy prostheses.

In another embodiment of the application of the process in accordance with the invention it may however occur that the layer of alumina 33 has a thickness greater than the previously fixed limit of approximately 50 microns.

Indeed, in an advantageous and unexpected manner, a thick layer of alumina 33 can be machined, which has the advantage of being able to create a special roughness on all or part of a prosthesis element. The plate 35 which covers and rings the prosthesis can, for example, be polished which improves the implantation of the prosthesis 1 in the osseous or periodontal medium. It is of course a special case of machining, but all types of roughness can be created within the limits of previously mentioned thickness for the layer of aluminum and the layer of alumina.

In this respect, the collection of a plate 35 in an insulated material such as alumina avoids the frequent oxidation of the pivot 3 at the level of this plate 35 when the prosthesis 1 is made of titanium alloy. The contact with the oxygen in the air present at this part of the prosthesis 1 makes this area very sensitive to such oxidation which is responsible for a number of failures in dental implantology. A prosthesis 1 made according to the process described in the invention thus offers large guarantees of resistance to external chemical attacks.

Another variant of the process in accordance with the invention consists int hat nickel 36 can be deposited on the core 31 of the pivot 3 prior to the deposit of aluminum. The nickel is thin compared with the thickness E of the layer of alumina 33.

This possibility, known in itself for the "hard" chromation, possibly increases the adherence of the intermediate layer of aluminum 34 and therefore of the layer of alumina 33, on the core 31. There is a less severe transition between the interatomic distances of the conductive material forming the core 31 and the aluminum of the intermediate layer 34.

It is obvious that neither the process in accordance with the invention nor the resulting prosthetic elements 1 are limited by the special measures previously described and that all the technical equivalents or equivalent processes that might be used in the spirit of the invention would not exceed its scope. The field of the invention is that of the dental or maxilo-facial restauration by means of simple or complex prostheses which are sealed and insulated against electrical effects due to the presence of different conductors in the biological medium in which the said prostheses are implanted.

We claim:

1. A process for making a dental or maxillo-facial prosthesis comprising depositing, by electrochemical deposition of pure aluminum with a non-aqueous electrolyte base having an aluminiumorganic complex bath, a layer of pure aluminum on a conductive substrate, the substrate comprising a core of the prosthesis, and oxidizing the layer of aluminum by anodization to obtain a layer of alumina.

2. The process of claim 1, wherein the oxidizing of the layer of aluminum comprises partially oxidizing the layer of aluminum retaining a layer of aluminum between the core and the layer of alumina.

3. The process of claim 1, wherein the oxidizing of the aluminum comprises hard anodization.

4. The process of claim 1, wherein the oxidizing of the aluminum comprises chromic or sulphuric anodization.

5. The process of claim 4, wherein, following the oxidation of the aluminum, the alumina is hydrated.

6. The process of claim 1, wherein the thickness of the layer of alumina is about 50 microns.

7. The process of claim 1, comprising, prior to the deposit of the aluminum, depositing on the core a layer of nickel.

8. The process of claim 7, wherein the layer of nickel is thinner than the layer of alumina.

9. The process of claim 1, wherein the prosthesis comprises an endo-osseous implant.

10. The process of claim 1, wherein the prosthesis comprises a pivot.

11. The process of claim 1, wherein the core of the prosthesis comprises metal.

12. A prosthesis manufactured by the process of claim 1.

13. The prosthesis according to claim 12 comprising an endo-osseous implant.

14. The prosthesis according to claim 12 comprising a pivot.

15. A dental or maxillo-facial prosthesis comprising a conductive substrate comprising a core of a prosthesis, a layer of pure aluminum on said core, and a layer of pure alumina on said layer of pure aluminum.

16. The prosthesis of claim 15 wherein said layer of pure alumina is about 50 microns.

17. The prosthesis of claim 15 comprising a layer of nickel between said core and said layer of aluminum and said layer of alumina.

18. The prosthesis of claim 15, wherein the core comprises metal.

19. The prosthesis of claim 15 comprising a pivot.

20. The prosthesis of claim 15 comprising an endoosseous implant.

* * * * *